United States Patent [19]
Chriswell et al.

[11] Patent Number: 5,478,452
[45] Date of Patent: Dec. 26, 1995

[54] IN SITU ISOLATION OF VOLATILE ORGANIC COMPOUNDS FROM GROUNDWATER

[75] Inventors: Colin D. Chriswell, Slater; John J. Richard, Ames, both of Iowa

[73] Assignee: Iowa State University Research Foundation, Inc., Ames, Iowa

[21] Appl. No.: 331,000

[22] Filed: Oct. 28, 1994

[51] Int. Cl.$^6$ ................................................. G01N 27/26
[52] U.S. Cl. ...................... 204/153.2; 73/19.01; 73/19.1; 73/23.2; 204/129; 204/153.1; 204/266; 204/400; 436/153; 436/154
[58] Field of Search ............................ 204/153.2, 153.1, 204/400, 129, 130; 73/19.01, 19.1, 23.2; 436/153, 154

[56] References Cited

U.S. PATENT DOCUMENTS

| | | | |
|---|---|---|---|
| 3,003,932 | 10/1961 | Frey et al. | 204/431 |
| 3,086,924 | 4/1963 | Bentley et al. | 204/430 |
| 4,572,582 | 2/1986 | Ryeczek | 166/248 |
| 5,256,264 | 10/1993 | Hundenborn et al. | 204/130 |

OTHER PUBLICATIONS

W. Bertsch et al., "The Determination of Organic Volatiles in Air Pollution Studies: Characterization of Profiles", *J. Chromatogr. Sci.*, 12 175 (1974) month unavailable.

C. D. Chriswell et al., "Use of Electrolytically Generated Hydrogen as a Purge Gas for the Isolation of Volatile Organic Compounds from Groundwater," *Separation Sci. and Tech.*, 28, 2377 (Nov. 1993).

C. D. Chriswell et al., "Selective Concentration of Amines From Aqueous Solutions by a Gas Purging Technique", *J. Chromatogr.*, 136, 371 (1977) month unavailable.

"Guidelines Establishing Test Procedures for the Analysis of Pollutants: Method 624—Purgables", in *40 Code of Federal Regulations, Part 136, Appendix A, Method 624*, Office of the Federal Register, National Archives and Records Administration, Washington, D.C., 1988 month unavailable.

"National Primary Drinking Water Regulations, Analysis of Trihalomethanes: Part I—The Analysis of Trihalomethanes in Drinking Water by the Purge and Trap Method", in *40 Code of Federal Regulations, Part 141, Subpart C, Appendix C*, Office of the Federal Register, National Archives and Records Administration, Washington, D.C., 1988 month unavailable.

G. A. Robbins et al., "Use of Headspace Sampling Techniques in the Field to Quantify Levels of Gasoline Contamination in Soil and Ground Water", *Proceedings of Petroleum Hydrocarbons and Organic Chemicals in Groundwater*, National Water Well Association Conference of the NWWA/API, Houston, Tex., 307 (Nov. 1987).

V. D. Roe et al., "Manual Headspace Method to Analyze for the Volatile Aromatics of Gasoline in Groundwater and Soil Samples", *Anal. Chem.*, 61, 2584 (1989) month unavailable.

*Test Methods for Evaluating Solid Waste*, vol. 1B, Chapter 4.2.1, Method 5030A, Laboratory Manual Physical/Chemical Methods, SW846, 3rd ed., U.S. EPA, Office of Solid Waste and Emergency Response, Washington, D.C., Nov., 1986.

B. A. Tompkins et al., "Determination of Regulatory Organic Compounds in Radioactive Waste Samples. Volatile (List continued on next page.)

*Primary Examiner*—T. Tung
*Attorney, Agent, or Firm*—Schwegman, Lundberg, & Woessner

[57] ABSTRACT

Methods and apparatus for in sire isolation of volatile organic compounds from groundwater using electrolytically-generated purge gas are disclosed. One preferred method includes electrolytically generating a purge gas from the ground water, passing the purge gas through the groundwater (in situ) to purge volatile organic compounds from groundwater, collecting the purge gas along with the purged volatile organic compounds, and detecting (in situ) the presence and/or amount of purged volatile organic compounds in the purge gas. One preferred apparatus includes a generally cylindrical cell incorporating the necessary electrodes, one or more ionization sources and detectors.

20 Claims, 2 Drawing Sheets

OTHER PUBLICATIONS

Organics in Aqueous Liquids", *Anal. Chem.*, 61, 2751 (1989) month unavailable.

A. Zlatkis et al., "Profile of Volatile Metabolites in Urine by Gas Chromatography—Mass Spectrometry", *Anal. Chem.*, 45, 763 (1973) month unavailable.

M. A. Baim et al., "Ion Mobility Detector for Gas Chromatography with a Direct Photoionization Source," *Anal. Chem.*, 55, 1761–1766 (1983) month unavailable.

T. A. Bellar, "Method 503.1. Volatile Aromatic and Unsaturated Organic Compounds in Water by Purge and Trap Gas Chromatography, Revision 2.0" Environmental Monitoring Systems Laboratory, Office of Research and Development, U.S. Environmental Protection Agency, pp. 63–87 (1989) month unavailable.

G. A. Cutter et al., "Determination of Dissolved Sulfide and Sedimentary Sulfur Speciation Using Gas Chromatography–Photoionization Detection," *Anal. Chem.*, 59, 717–721 (1987) month unavailable.

L. S. Cutter et al., "Simultaneous Determination of Inorganic Arsenic and Antimony Species in Natural Waters Using Selective Hydride Generation with Gas Chromatography/Photoionization Detection," *Anal. Chem.*, 63, 1138–1142 (1991) month unavailable.

W. Genuit et al., "Characterization of Beech Milled Wood Lignin by Pyrolysis–Gas Chromatography–Photoionization Mass Spectrometry," *Anal. Chem.*, 59, 508–513 (1987) month unavailable.

W. Nutmagul et al., "Photoionization/Flame–Ionization Detection of Atmospheric Hydrocarbons after Capillary Gas Chromatography," *Anal. Chem.*, 55, 2160–2164 (1983) month available.

H. Ogino et al., "Determination of Trace Impurities in High–Purity Oxygen by Gas Chromatography with Photoionization Detection," *Anal. Chem.*, 61, 2237–2240 (1989) month unavailable.

S. H. Vien et al., "Ultrasensitive, Simultaneous Determination of Arsenic, Selenium, Tin, and Antimony in Aqueous Solution by Hydride Generation Gas Chromatography with Photoionization Detection," *Anal. Chem.*, 60, 465–472 (1988) month unavailable.

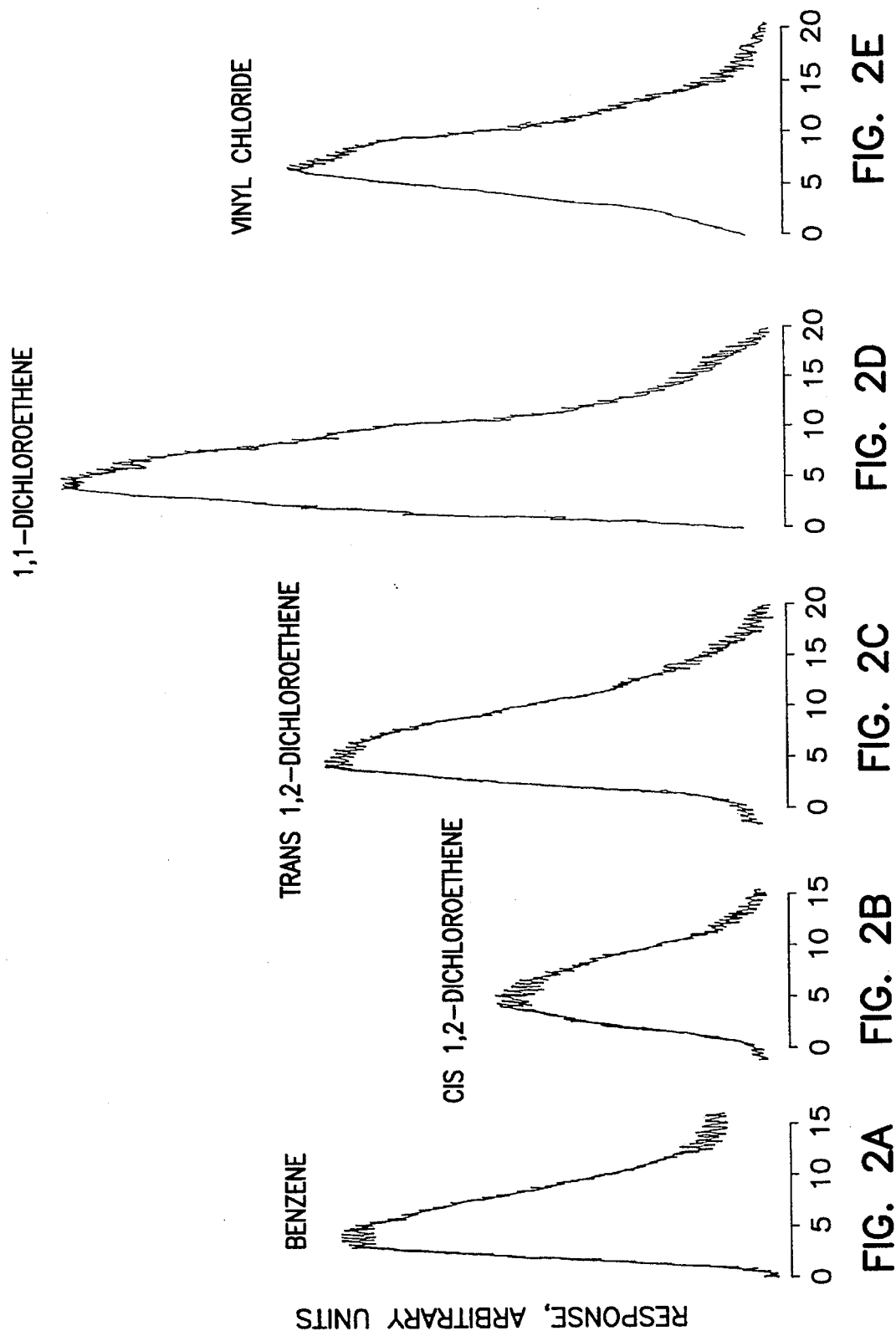

IN SITU ISOLATION OF VOLATILE ORGANIC COMPOUNDS FROM GROUNDWATER

STATEMENT OF U.S. GOVERNMENT RIGHTS

The U.S. Government has certain rights in this invention. This invention was made with U.S. Government grant support under DOE Contract No. W-7405-Eng-82.

FIELD OF THE INVENTION

The present invention relates to methods and apparatus for the isolation of volatile organic compounds. More particularly, the present invention relates to methods and apparatus for in situ isolation of volatile organic compounds from groundwater using an electrolytically-generated purge gas.

BACKGROUND OF THE INVENTION

Current methods and apparatus for the testing of groundwater for contamination are both time consuming and relatively expensive. Samples must be collected using methods which preserve their integrity, transported without affecting the composition of the sample and then analyzed in laboratories using equipment which is often more sensitive and elaborate than necessary to determine whether contamination exists. In addition such equipment is typically much more expensive to operate and the laboratories involved must pass on portions of their overhead when assessing charges for testing groundwater.

One alternative to collecting samples for laboratory analysis involves testing the air above groundwater, known as the headspace, for indications of hydrocarbon contamination. Typically, however, the level of groundwater contamination necessary to cause a measurable level of hydrocarbons in the headspace far exceeds acceptable groundwater contamination levels, this making this test method effective for only gross levels of contamination.

As a result, the testing of groundwater for contamination at acceptable levels is more expensive than is necessary and/or is also difficult from a logistic standpoint when using known techniques and equipment.

SUMMARY OF THE INVENTION

The present invention provides methods and apparatus for in situ isolation of volatile organic compounds from groundwater using electrolytically-generated purge gas. One preferred method according to the present invention includes electrolytically generating a purge gas from the ground water, passing the purge gas through the groundwater (in situ) to purge volatile organic compounds from groundwater, collecting the purge gas along with the purged volatile organic compounds, and detecting (in situ) the presence and/or amount of purged volatile organic compounds in the purge gas.

One preferred apparatus according to the present invention comprises a generally cylindrical cell incorporating the necessary electrodes, one or more ionization sources and detectors. Preferably, the cell is sufficiently small to be placed in sampling wells. Those cells which are destined for long term installation also preferably are fabricated from materials which resist corrosion and buildup of deposits which may adversely affect their ability to operate.

In one aspect, the present invention comprises the step of using electrolytically-generated hydrogen from the groundwater as the purge gas. In yet another aspect, the present invention comprises using electrolytically-generated oxygen as the purge gas.

In another aspect, the present invention comprises a method and apparatus in which the detection of volatile organic compounds is accomplished using two ionization sources to ionize the volatile organic compounds. By using two ionization sources operating at different energy levels, the present invention can provide a signal proportional to the concentration of volatile organic compounds.

One of the advantages of the method and apparatus according to the present invention is the ability to generate a purge gas, purge volatile organic compounds from groundwater and analyze the purge gas for volatile organic compounds–all in situ–without the need for taking samples and transporting them to laboratories.

Another advantage of the present invention is that only electricity be supplied to the monitoring cell. Furthermore, in some instances, the necessary electricity may be supplied by batteries.

Another advantage of the present invention is that the device and method can be used in conjunction with small diameter sampling wells, avoiding the need for additional drilling to provide access to the groundwater.

Yet another advantage according to the present invention is that existing mature technologies are used which increase the reliability and accuracy of results achieved using the method and apparatus according to the present invention.

Yet a further advantage of the present invention is that measurements of the volatile organic compounds are made, in the preferred method, in a hydrogen matrix which is free of the interfering species normally present in the groundwater.

Yet another advantage of the present invention is that the detection limits for volatile organic compounds are several orders of magnitude lower when those compounds are purged from water than when they are measured in the head space above samples as currently tested.

These and other features and advantages of the method and apparatus according to the present invention will become apparent upon a reading of the detailed description of the invention below along with reference to the drawings and claims.

BRIEF DESCRIPTION OF THE DRAWINGS

FIGS. 2A–2E depict actual response rates of various samples purged using a method and apparatus simulating the present invention.

DETAILED DESCRIPTION OF THE INVENTION

Figure 1:
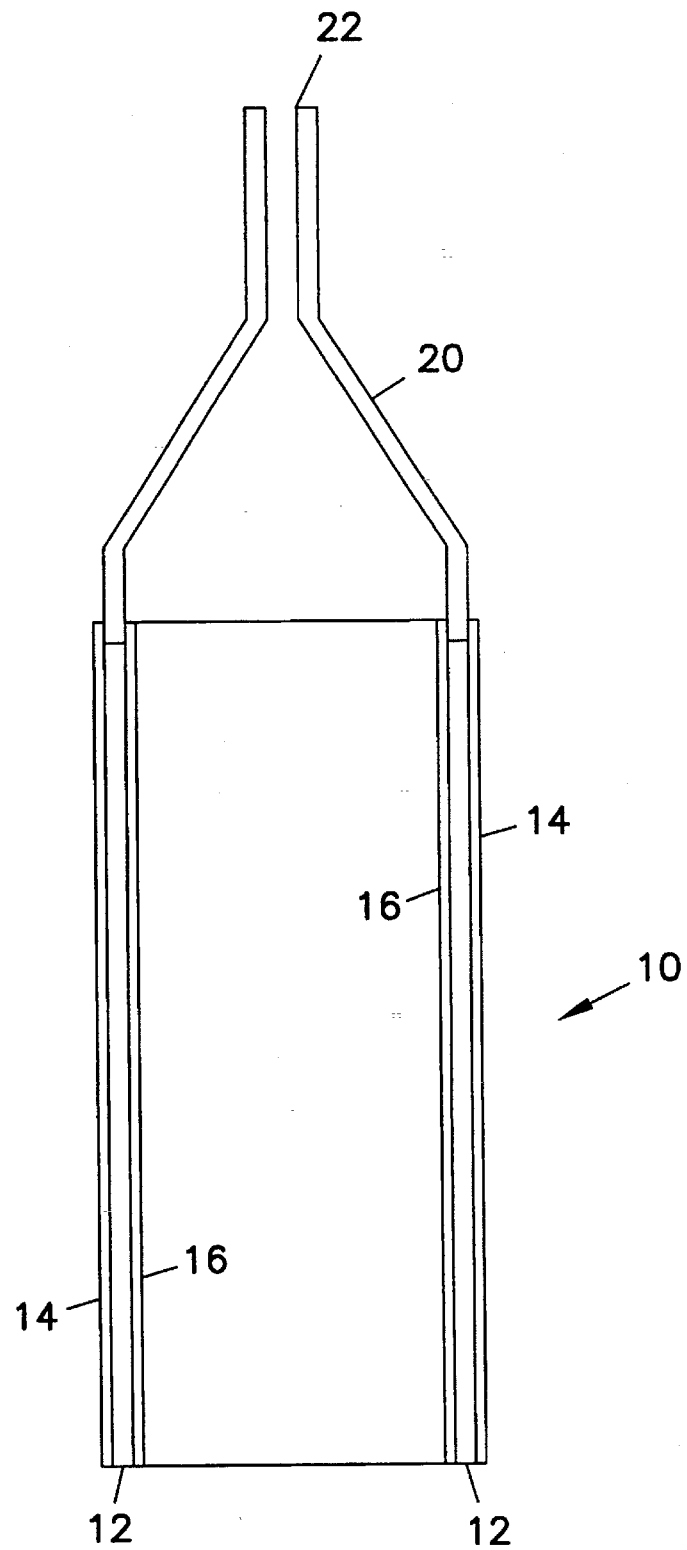
FIG. 1 is a schematic diagram of a cross-section of an electrolysis cell for use in the apparatus and methods according to the present invention.

The present invention comprises both a method and apparatus for in sire isolation and detection of volatile organic compounds in groundwater.

The method according to the present invention involves placing an electrolysis cell (which is described more fully below) within the groundwater to be tested. The preferred cell requires only electrical connections to carry a signal away from the cell and to provide power for the detector and electrodes needed for electrolytically generating the purge gas. Alternately, it will be understood that the power line may be optional in those cases where the cell itself is provided with batteries to power both the photoionization detectors as well as the electrodes for generating the purge gas.

Once in place, an electric potential is placed across the electrodes to electrolytically generate the purge gas which is then collected proximate the photoionization detectors. The detectors are energized to ionize the volatile organic compounds purged and return a signal to the user to allow monitoring of the levels of volatile organic compounds in the groundwater. The return signal can be output by any variety of means including a strip chart recorder, computer with data acquisition software and many other varieties of acquiring and recording data which will be well known to those skilled in the art.

As used in connection with the present invention, the term "volatile organic compounds" includes organic compounds having a boiling point of about 200° C. or less at standard temperature and pressure. More preferably, the organic compounds have a boiling point of about 150° C. or less at standard temperature and pressure.

In one preferred method which is described more fully below, the ionization process is conducted at two different energy levels to determine the concentration of certain types of volatile organic compounds within the groundwater.

Turning now to FIG. 1 in which a preferred embodiment of a cell according to the present invention is depicted, the cell 10 is comprised of a core of fiberglass cloth 12 sold commercially for automobile body repair (specify manufacturer and model or type of fiberglass cloth here) which acts as a spacer between an anode 14 surrounding the exterior of fiberglass cloth 12 and a cathode 16 placed within the inside diameter of the cylindrical fiberglass cloth 12.

The cathode 16 was placed within the spacer 12 became the preferred purge gas was hydrogen which is generated at the cathode during water electrolysis. The present invention can, alteratively, involve the use of oxygen as the purge gas, in which case the anode and cathode positions would be reversed so that the oxygen would pass through the water within cell 10 and be collected for analysis.

The preferred anode 14 comprises a layer of 20 mesh stainless steel screening material while the preferred cathode 16 comprises a layer of 20 mesh nichrome screening material. It will be understood that many other electrically conductive materials could be substituted for the preferred stainless steel and nichrome electrode materials. Examples of some materials which could be substituted include platinum or nickel.

The use of stainless steel for the anode 14 and nichrome for the cathode 16 was preferred to reduce the dissolution of electrode materials and the formation of flocculent precipitates which can foul the cell 10 and reduce the accuracy of the device.

Considerations which went into selection of the fiberglass cloth 12, which serves as the spacer between the anode and cathode, were stability and permeability to ions. One alternative identified is chamois leather which appeared to provide a sufficiently stable spacer which was also permeable to ions passing between the anode and cathode. In addition to the preferred fiberglass cloth and chamois leather, it is envisioned that other materials could also be substituted for the spacer material 12 used between the anode 16 and cathode 14 in apparatus according to the present invention.

Returning to FIG. 1, the preferred cell 10 includes a funnel 20 or other gas collection device above the anode 14 and cathode 16 of cell 10. In the test device, a polypropylene Buchner funnel was placed on top of the cylindrical portions of the cell 10 to collect the purge gas and associated volatile organic compounds purged from the groundwater.

The constricted opening 22 from the funnel is placed as shown to allow the purge gas to escape at a controlled rate. It will be understood that the collector 20 could be provided in any number of geometric shapes with the primary requirement being relative impermeability to the purge gas and a shape which captures substantially all of the purge gas and associated volatile inorganic compounds purged from the groundwater within cell 10.

The photoionization detector was mounted on the collector 20 and was directed into the area enclosed by the collector and in which the purge gas and volatile organic compounds were contained. The preferred detector was an HNU model PI-52-02 photoionization detector. In most studies, a standard 10.2 eV lamp was used to perform the photoionization. Where a second signal was necessary, an 11.7 eV lamp was used to provide a signal to compare with that generated when the 10.2 eV lamp was used. In one preferred embodiment, two detectors would be used each supplied with the appropriate lamp. Output from the detector was recorded using a strip chart recorder (Fisher Series 5000) although many other methods of providing output could be used as described above.

In the preferred embodiment and method, a power supply was connected to the anode and cathode which provided 30 or 60 volts across the spacer 12. The preferred power supply provided DC voltage k is also envisioned that batteries could be used in place of an external power supply which would provide the additional advantage of limiting the connection to cell 10 to a signal line. The exact voltage used across the cathode 16 and anode 14 is unimportant provided that sufficient voltage is supplied to electrolytically generate the purge gas. It should be understood, however, that a larger potential should limit the effects of the variations in ionic strength of the groundwater.

In that regard, different samples of water were tested to determine the effect of ionic strength in the rate at which hydrogen is generated and, therefore, also effective rate at which the volatile organic compounds were purged from the water. The results of that analysis indicated that voltage between the anode and cathode should be kept sufficiently high to minimize variations in the ionic strength of the water.

Another factor to consider when designing a cell 10 and test protocols for determining the presence of volatile organic compounds is the thickness and porosity of the spacer 12 used between the anode and cathode. Limiting factors in the choice of spacers include thickness and porosity which can affect the peak signals detected by the detector as well as the length of time needed to strip the volatile organic compounds from the groundwater in cell 10.

One factor also considered is the buildup of salts on the fiberglass spacer 12 and adjacent cathode 16 surface. Prolonged use may result in calcium carbonate and iron hydroxide being deposited in the spacer and on the cathode surface adjacent to the spacer. Those depositions may reduce the rate of diffusion through the cell 10 and change the oilrating characteristics of the cell 10. These effects may be particularly noticeable where cell 10 was used as an unattended in situ monitor in goundwater containing high levels of calcium carbonate or iron. In those situations, a more porous spacer may be necessary to reduce the effects of deposits on the cathode surface as well as within the spacer 12.

Tests were conducted using the preferred embodiment of the cell 10 as described above to determine its detection limits. The preferred cell has a detection limit of less than five parts per billion (ppb) for benzene and for 23 other organic compounds tested, response factors ranged from 0.1 to 1.5 times that for benzene. One particular use for which the present invention is well suited is for monitoring the concentration of gasoline in groundwater in the vicinity of underground storage tanks. The tests were conducted under conditions controlled to verify the device's ability to detect the tested compounds. Cell 10 was immersed in 325 ml of water in a 400 ml beaker and voltage was supplied to the electrodes. The electrolysis cell 10 was connected to the preferred photoionization detector using PTFE tubing, although it will be understood that in a commercial embodiment, the detector must only be connected in a way in which the purge gas is sufficiently entrapped to provide for ionization and detection of the resulting signal.

After the electrodes were energized, the cell produced electrolytically generated hydrogen which then flushed any air in the system from cell 10. After the system had stabilized, a volume of a methanol solution of the desired test compound was injected into the 325 ml of water to produce a concentration of 50 micrograms per liter (ppb) in the water. Purging was then allowed to proceed for about 10 to 20 minutes until all of the analyte had been stripped from the sample and a stable baseline was reestablished in the signal from the photoionization detector.

Table 1 shows the relative response factors and purge times for a variety of compounds which were provided according to the test protocol described above at concentrations of 50 ppb. These compounds were detected using a 10.2 eV photoionization detector and are compared to the baseline established for benzene. The relative purge time factor is an indication of the time required for the maximum signal to be obtained as compared to the time required for the maximum signal for benzene.

TABLE 1

Relative Response Factors and Purge Times for Compounds Present in Water at 50 ppb Isolated Using Electrolytically Generated Hydrogen and Detected Using a 10.2 eV Photoionization Detector

| Compound | Boiling Point, °C. | Relative Response Factor | Relative Purge Time |
| --- | --- | --- | --- |
| Bromoform | 150 | 0.3 | 0.8 |
| Bromomethane | 4 | 0.1 | 0.8 |
| Chlorobenzene | 132 | 0.6 | 0.9 |
| Chloroethyl Vinyl Ether | 109 | 0.7 | 0.8 |
| Cyclohexane | 81 | 0.9 | 0.8 |
| Dibromochloromethane | 120 | 0.2 | 0.9 |
| 1,2-Dichlorobenzene | 179 | 1.2 | 0.8 |
| 1,3-Dichlorobenzene | 172 | 1.0 | 0.8 |
| 1,1-Dichloroethene | 30 | 3.0 | 1.0 |
| cis-1,2-Dichloroethene | 60 | 0.9 | 0.9 |
| trans-1,2-Dichloroethene | 48 | 2.1 | 0.9 |
| 1,2-Dichloroethene (80% trans, 20% cis) | — | 1.7 | 1.0 |
| 1,2-Dichloropropene | 75 | 0.6 | 0.7 |
| 1,3-Dichloropropene | 106 | 0.6 | 0.9 |
| Gasoline | — | 1.5 | 0.9 |
| n-Heptane | 98 | 1.3 | 0.8 |
| Isooctane | 98 | 1.2 | 0.8 |
| Tetrachloroethene | 121 | 0.7 | 0.9 |
| Thiophene | 84 | 1.0 | 1.0 |
| Toluene | 111 | 1.1 | 1.1 |
| Trichloroethane | 87 | 1.0 | 0.9 |

TABLE 1-continued

Relative Response Factors and Purge Times for Compounds Present in Water at 50 ppb Isolated Using Electrolytically Generated Hydrogen and Detected Using a 10.2 eV Photoionization Detector

| Compound | Boiling Point, °C. | Relative Response Factor | Relative Purge Time |
| --- | --- | --- | --- |
| Vinyl Chloride | −14 | 1.2 | 0.7 |
| Xylene | 137 | 1.1 | 1.8 |

In addition to the compounds shown, other compounds were tested but were either unable to be purged from the water or, in the alterative, were not ionized by the 10.2 eV photoionization source. Typically, a 10.2 eV source has insufficient energy to efficiently ionize most aliphatic compounds having four or less carbon atoms and their halogenated homologues.

One alterative to remote testing of groundwater samples is the testing of air in the head space above groundwater as an indication of the hydrocarbon contamination of the groundwater. Typically, however, head space testing is incapable of detecting benzene at concentrations of up to 1000 ppb, whereas current regulations require remediation when groundwater contains more than 50 ppb of benzene. As a result, head space analysis is typically able to detect only severely contaminated groundwater.

Tests were also conducted to determine the effects of other variables on the performance of the present invention. Experimental curves, depicted as FIGS. 2A–2E were obtained by providing benzene (FIG. 2A) and four chlorinated hydrocarbons at 50 ppb in samples of water and purging the samples according to the present invention. Small differences in the shape of the curves can be attributed to differences in the rate of diffusion of the compounds into the cell as well as the rate at which the compounds are purged from water.

A potential additional use of the present invention lies in the stripping of compounds from groundwater using electrolytically-generated purge gas. Tests conducted included immersing a cell (not shown) constructed according to the present invention in 16 liters of water containing benzene at a concentration of 62 ppb. All benzene was depleted from the water after 9 hours of operation, thereby demonstrating that the present invention may also be useful as a remediation tool for contaminated groundwater.

Although specific methods and examples have been illustrated and described herein, it will be appreciated by those of ordinary skill in the art that any arrangement which is calculated to achieve the same purpose may be substituted for the specific methods and examples described. This application is intended to cover any adaptations or variations of the present invention. Therefore, it is manifestly intended that this invention be limited only by the claims and the equivalents thereof.

We claim:

1. A method for in situ isolation of volatile organic compounds from groundwater comprising the steps of:

a) electrolytically generating a purge gas from groundwater, in situ;

b) purging volatile organic compounds from the groundwater with the electrolytically generated purge gas in situ;

c) collecting the purge gas in situ along with the purged volatile organic compounds; and d) detecting the presence of purged volatile organic compounds in the purge gas in situ.

2. A method according to claim 1, wherein the volatile organic compounds have a boiling point of about 200° C. or lower.

3. A method according to claim 1, wherein the volatile organic compounds have a boiling point of about 150° C. or lower.

4. A method according to claim 1, wherein the step of electrolytically generating the purge gas comprises:
   1) providing an anode and cathode in situ within the groundwater;
   2) holding the anode and cathode at different electric potentials to generate hydrogen and oxygen through breakdown of the groundwater.

5. A method according to claim 1, wherein the step of detecting comprises:
   1) ionizing the purged volatile organic compounds with an ionization source;
   2) generating a signal corresponding to the amount of purged volatile organic compounds ionized by the ionization source.

6. A method according to claim 5, wherein the step of ionizing comprises photoionization.

7. A method according to claim 1, wherein the step of detecting comprises:
   1) ionizing the purged volatile organic compounds with a first ionization source;
   2) generating a first signal corresponding to the amount of purged volatile organic compounds ionized by the first ionization source;
   3) ionizing the purged volatile organic compounds with a second ionization source;
   4) generating a second signal corresponding to the amount of purged volatile organic compounds ionized by the second ionization source; and
   5) comparing the first and second signals to determine a concentration level of a desired group of volatile organic compounds.

8. A method according to claim 7, wherein the first and second ionization sources operate at different energy levels.

9. A method according to claim 7, wherein the second ionization source operates at a higher energy level than the first ionization source.

10. A method according to claim 1, wherein the purge gas comprises hydrogen.

11. A method according to claim 1, wherein the purge gas comprises oxygen.

12. A method for in situ isolation of volatile organic compounds from groundwater comprising the steps of:
   a) providing an anode and cathode in situ within the groundwater;
   b) holding the anode and cathode at different electric potentials to generate a purge gas comprising hydrogen through breakdown of the groundwater;
   c) passing the purge gas through groundwater, in sire, to purge volatile organic compounds from the groundwater;
   d) collecting the purge gas in situ along with the purged volatile organic compounds;
   e) detecting the presence of purged volatile organic compounds in the purge gas in sire by:
   1) ionizing the purged volatile organic compounds with a photoionization source:
   2) generating a signal indicative of the presence of the purged volatile organic compounds in the purge gas.

13. A method according to claim 12, wherein the volatile organic compounds have a boiling point of about 200° C. or lower.

14. A method according to claim 12, wherein the volatile organic compounds have a boiling point of about 150° C. or lower.

15. An apparatus for in sire isolation of volatile organic compounds from groundwater comprising:
   a) a cathode and anode located in sire in the groundwater;
   b) a voltage source connected to the anode and cathode for holding the anode and cathode at different electric potentials to facilitate the breakdown of groundwater into hydrogen and oxygen for use as purge gas;
   c) means for collecting the purge gas in situ after it has passed through the groundwater;
   d) means for detecting the presence of volatile organic compounds in the purge gas in situ.

16. An apparatus according to claim 15, wherein all components of the apparatus are contained in a cell capable of fitting within a circular opening having a diameter of about one inch or less.

17. An apparatus according to claim 15, wherein the voltage source comprises batteries located proximate the anode and cathode.

18. An apparatus according to claim 15, wherein the means or detecting comprises means for ionizing the volatile organic compounds in situ.

19. An apparatus according to claim 18, wherein the means for ionizing comprises a photoionization detector.

20. An apparatus for in situ isolation of volatile organic compounds from groundwater comprising:
   a) a cell capable of fitting within a circular opening having a diameter of about one inch or less, the cell capable of being located within groundwater;
   b) a cathode and anode proximate the cell;
   c) a voltage source connected to the anode and cathode for holding the anode and cathode at different electric potentials to facilitate the breakdown of groundwater into hydrogen and oxygen for use as purge gas;
   d) means for collecting the purge gas in the cell after the purge gas has passed through the groundwater;
   e) a photoionization detector for detecting the presence of volatile organic compounds in the purge gas in the cell.

* * * * *